(12) United States Patent
Costa et al.

(10) Patent No.: US 7,438,928 B2
(45) Date of Patent: Oct. 21, 2008

(54) TOPICAL GEL MATRIX

(75) Inventors: Anthony Costa, Laval (CA); Benoit Choquet, Longueuil (CA); Yvan Giguère, Montreal (CA)

(73) Assignee: Rolf C. Hagen, Inc., Quebec (CA)

( * ) Notice: Subject to any disclaimer, the term of this patent is extended or adjusted under 35 U.S.C. 154(b) by 527 days.

(21) Appl. No.: 10/685,685

(22) Filed: Oct. 15, 2003

(65) Prior Publication Data

US 2004/0115228 A1    Jun. 17, 2004

Related U.S. Application Data

(60) Provisional application No. 60/418,726, filed on Oct. 17, 2002.

(51) Int. Cl.
*A61K 9/14* (2006.01)

(52) U.S. Cl. .................................................. 424/486

(58) Field of Classification Search ....................... None
See application file for complete search history.

(56) References Cited

U.S. PATENT DOCUMENTS

| | | | |
|---|---|---|---|
| 4,551,332 A * | 11/1985 | Stillman | .................. 424/401 |
| 4,729,190 A * | 3/1988 | Lee | ........................... 47/57.6 |
| 5,019,604 A | 5/1991 | Lemole | .................... 523/105 |
| 5,573,756 A * | 11/1996 | Lambrechts | ............ 424/70.24 |
| 6,074,438 A * | 6/2000 | Lim et al. | ...................... 8/409 |
| 6,447,788 B1 * | 9/2002 | Strathausen | ................ 424/401 |

FOREIGN PATENT DOCUMENTS

EP          625034          6/2002

OTHER PUBLICATIONS

Aculyn-44 disclosure, published by Rohm and Haas, downloaded from the world wiide web on Apr. 30, 2007.*

* cited by examiner

*Primary Examiner*—Michael G. Hartley
*Assistant Examiner*—Eric E Silverman
(74) *Attorney, Agent, or Firm*—Schnader Harrison Segal & Lewis LLP

(57) ABSTRACT

A topical gel matrix that can be used alone or combination with a medication entrapped therein. The gel matrix is dispersible in water. The gel may have the following composition: oil, water or aqueous solution; solvents, surfactants and/or detergents; and a polymer which is a consistence modifier capable of thickening and to resist degradation in a water environment. The matrix may comprise or not a biologically active ingredient for a systemic or topical indication. Amongst preferred medications are anaesthetic, anti-histaminic, anti-inflammatory, anti-oxidant, anti-UVs, anti-microbial and wound healing agents. More specifically, for the treatment of fish infections, examples of preferred active ingredients are natural or synthetic plants extracts.

19 Claims, No Drawings

TOPICAL GEL MATRIX

CROSS REFERENCE TO RELATED APPLICATIONS

This application claims priority on U.S. provisional application No. 60/418,726, filed on Oct. 17, 2002, now expired. All documents above are herein incorporated by reference.

FIELD OF THE INVENTION

This invention relates to a gel matrix to be applied topically at the surface of a subject's mucosa, mucus or skin. It more particularly relates to a water insoluble water dispersible matrix comprising a viscosity enhancer polymer.

BACKGROUND OF THE INVENTION

Medications that are available on the veterinary market for treating infections, particularly in fish, are chemicals like formaldehyde or malachite green. Although efficient, these chemicals have the disadvantage of providing undesirable or toxic side effects. The mode of administration is also not ideal. The injured fish may be soaked in a medicated bath unnecessarily for a topical injury and, this may be even undesirable because of its systemic effects (the fish ingests the medication when a topical effect is sought). Alternatively, a local application can be made: the fish is netted, positioned and localized lesions are quickly sprayed with the chemical mixture. The fish is usually rinsed off in a container of water before being returned to a tank or to its aquarium. The objective is to keep the contact time of the fish with the chemical mixture as short as possible to avoid necrosis or burns. Some antibiotics and steroids administered that way may be efficient although their contact time with the skin is relatively short. Another drawback of the topical application as it now exists is that there is a loss of medication which goes into the rinsing water and that is not used for the treatment per se. There is certainly a need to improve and to maximize the contact time of a medication with minimal loss and toxicity.

A first type of skin adhesive gel has been described in EP 625, 034. These gels are water-insoluble but water-swellable cross-linked ampholyte salts of PVP and amines. These hydrogels may be coated with a urethane film backing to control the moisture vapour transmission rate. There is no disclosure of an urethane gel itself serving as an adhesive drug-releasing matrix further having the property of being water-dispersible.

Another type of protective gel is disclosed in U.S. Pat. No. 5,019,604. This gel is intended to be used for covering surgeons' hands together with standard surgical gloves. The gel is mainly composed of lanolin, silicone, a surfactant and polytetrafluorethylene powder used as a water repellent. The gel is removable with alcohol and surfactants, and thus does not appear to be water dispersible. For treating fishes, water dispersibility is necessary for recovery of a healthy state.

Furthermore, the treatment of infectious diseases, specifically in fishes, would benefit from finding any new compound, preferably of a natural origin, which would be innocuous.

Combining an efficient and safe compound with a new delivery matrix would further reduce the need for quarantines and would minimally affect the quality of the water environment.

SUMMARY OF THE INVENTION

The invention relates to a gel matrix to be applied topically at the surface of a subject's mucosa or skin. It more particularly relates to a water insoluble water dispersible matrix comprising a viscosity enhancer polymer. It may further comprise essential oils, surfactants and solvents. The polymer allows the gel matrix to be viscous and sprayable and, at the same time, it creates a <<bandage>>effect when sprayed on a surface. The gel matrix may comprise any medication, for use in topical treatment. Namely a plant oil extract such as Sweet Birch oil for use in fish topical treatment has been produced. The gel matrix can incorporate any other medication including essentials oils derived from plants, seeds, herbs and spices.

In accordance with the invention, there is provided a gel matrix for topical use on a subject having an epithelial surface to be immersed in water, the epithelial surface comprising mucus, mucosa or skin surface, the gel matrix being insoluble but dispersible in water, comprising:
- a polymer that confers to said matrix the characteristics of being insoluble but dispersible in water, and which is capable of adhering to said surface,
- a liquid carrier which is bio-compatible with the surface, the gel matrix having a viscosity before application of about 50 centipoises.

The polymer may be polyurethane, more specifically a nonionic hydrophobically modified ethoxylated polyurethane. In a specific embodiment it is a polyethylene glycol-150/decyl alcohol/saturated dicyclohexyl-methane diisocyanate (SMDI) copolymer, sold under the trademark ACULYN 44™.

The gel matrix may further comprise a medication, for systemic or topical use. Preferably, the medication is active towards any causative agent or symptom affecting the surface.

The medication can be selected from anti-ulcer, anti-microbial, anti-infectious, anti-histaminic, anti-inflammatory, soothing, wound healing, sun screen, anti-UVs, anti-cancer, anesthetic and analgesic agents.

Preferred medications are organic oils, namely plant oil extracts. Against infectious agents, plant oil extracts having anti-infectious properties have been particularly preferred. When the subject to be treated is a fish, the preferred oil is pine, clove, coriander or Sweet Birch oil, in a final concentration of 1-5% (w/w). When oils are present, the gel may further comprise an anti-oxidant to avoid lipid degradation.

A concentration of about 15% (w/w) ACULYN 44™ is adequate to achieve the desired viscosity. Besides the polymer, the gel may further comprise 32-45% glycol-comprising phase and 40-53% aqueous phase. The glycol phase comprises the oil and surfactant components, or more hydrophilic components.

A gel matrix having the following composition has been made for topical use:
ACULYN 44™ 15%, ethoxydiglycol 34-45%, oil 1-5%, polysorbate 20 (sold under the trademark LIPOSORB L-20™) 1-6%, demineralised water 41.17%, propyl gallate 0.1%, sodium metabisulfite 0.25%, sodium carbonate 0.05% and dye yellow 5 LK (14-16%) 0.50%. In a specific embodiment, the oil was Sweet Birch oil.

As used herein the term "mucosa" is meant to refer to the inner surface of tubular structures and hollow organs, comprising a superficial epithelial membrane which is lubricated by mucous and rests upon a basal lamina which is supported by a layer of connective tissue, the lamina propria. Without being so limited it includes the skin of fishes and amphibians, the luminal surface of organs including the mouth, nose, vagina, cloaca and the gastrointestinal system.

As used herein the term "mucus" is meant to refer to the viscid, watery secretion that covers mucosa.

DESCRIPTION OF THE INVENTION

In their search for a non-toxic formulation to treat fish, the applicants have focused on the development of a matrix that would improve drug release and on finding a non-toxic natural plant extract that would be relatively innocuous in the active dosage range.

The matrix itself provides for a drug delivery system and a physical barrier to prevent infection from the infected or wounded subject's skin or mucosa to its environment, or conversely, from the environment (which is never aseptic) to the injured subject. The matrix is a gel that is slowly dispersible in water, therefore having a contact time long enough to protect the skin and, if comprising a medication, to allow slow diffusion or release of the medication entrapped therein, with minimal loss and toxicity.

The matrix of course would find a vast panel of applications which are not restricted to a veterinary use and certainly not to infectious diseases, or fish treatment.

The gel may be sprayed in a liquid form, or applied precisely on a surface to treat with the tip of an applicator that has been dipped into the liquid. The carriers (spray or liquid) depend on the surface to treat and on the whole body surface of the subject. A spray would be a favorite form for large surfaces or large organisms while very small injuries or small animals will be treated with the applicator.

It is also possible to envisage a composition which would further comprise a solid support like a plaster. A plaster could comprise a reservoir space comprising the gel of the present invention. The gel can be sprayed onto the pad of a plaster, or the pad itself can be soaked and impregnated with the liquid. The plaster may be porous to air and water to help healing. On the contrary, the plaster may be impervious to air and water on at least a part of its surface, which would limit or inhibit the diffusion of a drug in the direction of the closed non-porous side and thereby orient the diffusion of the drug to the injured site in contact with the gel.

Although the gel is in constant contact with water, as it is slowly dispersible in water, it stays in contact with a treated surface (skin, mucus or mucosa) for a while as a viscous layer or plug.

Such a gel matrix would be particularly efficient to cover a scratched, burned, irritated or infected skin or mucosa surface of a patient who would be able to swim without an unpleasant sensation of burn caused by water, chlorine, salt or sun.

The gel would be used as is or in combination with any medication intended for systemic or topical absorption. Non-limitative examples of topical medications are either one or more of analgesic, anesthetic, anti-histaminic, anti-inflammatory, soothing, anti-oxidants, anti-UVs, anti-infectious, anti-microbial, anti-ulcer, anti-cancer or wound healing agents.

The gel is a matrix constituting a physical barrier and, if it comprises any pharmacological agent, it constitutes both physical and chemical barriers to a pathogen or to an irritating environment, as well as it is a drug delivery system for the medication. The injured site becomes <<isolated>> from its environment during the period where the gel remains in place so as to cover the wounded area for maximal recovery.

A medication to be used for the treatment of fish infections would desirably be innocuous and efficient toward a broad range of pathogens (including *Pseudomonas fluorescens* and *Pseudomonas aeruginosa*). Sweet Birch oil, an aromatic oil comprising methyl salicylate and cresols as active ingredients, satisfies these criteria. Other plant oil extracts were also tested with success as ingredients of interest: pine, clove and coriander extracts. The oils are effective at least in concentrations of 1-5% (w/w).

A gel composition would comprise:
an oil, water or aqueous solution
anti-oxidants for protecting oil components, if any,
solvents, detergents and/or surfactants to dissolve other components (hydrophilic and hydrophobic),
a polymer which is a consistency modifier admixed to the oil, water or aqueous solution. ACULYN 44™ is a specific example of such of polymer. It is a nonionic rheology modifier based upon Hydrophobically modified Ethoxylated Urethane (HEUR) chemistry, providing benefits to formulations like thickening, stabilization and suspension. The polymer further contributes to adherence to skin, mucus or mucosa. Any other polymer biologically compatible with epithelial surfaces and having a consistency modifier capacity equivalent to that of ACULYN 44™, and more specifically to 15% ACULYN 44™, is considered to be within the scope of this invention.

A more specific composition would comprise:
15% ACULYN 44™
32-45% glycol (a phase comprising a solvent such as ethoxydiglycol)
40-53% aqueous phase.

The glycol solvent would be selected as one capable of dissolving oil therein and of providing a solution when further mixed with an aqueous solution.

A specific composition is the following (per 100 g):
PART A: Aqueous phase
41.17 g demineralised water
g propyl gallate
0.25 g sodium metabisulfite
0.05 g sodium carbonate
0.50 g dye yellow 5 LK 14-16%

In a clean suitable container equipped with a lightening type mixer add the required amount of water. Begin vigorous agitation and add propyl gallate and sodium metabisulfite. Mix for 45 minutes to 1 hour till dissolution. Proceed to add the sodium carbonate and mix till all dissolved. Then add the dye FD&C Yellow NO. LK 14-16% with mixing. Mix Part A for another 10-15 minutes. The dye has for purpose to make the site of application easily visible.

PART B: Glycol Phase
(1) 3 g LIPOSORB L-20™ (polysorbate 20)
(2) 2.5 g Oil (ex: Sweet Birch oil)
(3) 37.4 g ethoxydiglycol (sold under the trademark TRIVALIN SF™). Trivalin SF™ (ethoxydiglycol)

In a separate suitable container equipped with an appropriate mixer add LIPOSORB L-20™ then add the Sweet Birch oil with mixing. Mix till all the Sweet Birch oil has gone in solution. Then add TRIVALIN SF™ and mix till Homogeneous. The proportions of (1), (2) and (3) may be varied from 1-6%, 1-5% and 34-45%, depending on the oil content and hydrophobicity. When no lipid is added, the surfactant and ethoxydiglycol contents are decreased so as to reach a viscosity of about 50 centipoises.

Add PART A to PART B and mix for 15 to 20 minutes.

PART C: Add 15 g ACULYN™ * and mix until homogeneous liquid gel is obtained. Mix for another 10 minutes or so.

*ACULYN's 44™ composition: modified polyethylene glycol 34-36%, propylene glycol 38-40% and water 25-27%; purchased from Rohm and Haas Company.

The Sweet Birch oil is exemplified to provide an anti-infectious composition for fish. For other uses, it may be omitted or replaced by any other lipid or hydrophobic medication namely any aromatic compound of natural or synthetic origin having for example anyone of anti-ulcer, anti-microbial or anti-infectious (anti-viral, antibiotic, anti-fungal), anti-oxidant, soothing, anti-UVs, sun screen, anti-cancer, anti-histaminic, anti-inflammatory, anesthetic and/or analgesic properties.

An initial viscosity of about 50 centipoises (35-55 centipoises) is sought. As witnessed by the presence of the dye, the above composition stayed in contact with fishes' skin for a duration of at least 5 to 7 days.

The gel is kept in a non-porous container that is not attacked by any gel component and/or that does not allow oxygen permeation in quantities such that the lipids would be degraded or oxidized. Glass has been selected as a preferred type of container. Further the container should be capped adequately. An aluminum inner surface and plastic outer adhesive surfaces have been found to perform very well.

The ingredients are selected to be altogether non-soluble in water. The gel adheres to skin, mucosa or mucus; it slowly disperses in water, which increases the residence or contact time of a medication and avoids bathing the whole organ or organism (namely a fish) in a medication solution. The treatment is then focused, localized and requires less medication because there is a lesser loss of medication. It further decreases the need for quarantines and provokes fewer side effects. This route of administration insignificantly affects the aquatic environment.

Tests have been conducted with the above-preferred composition on freshly received fishes having different types of epizooties. At least 50% of the improvement in recovery from any skin lesions appears to be attributable to the matrix itself (comprising water instead of oil), the balance of effect being due to the presence of the Sweet Birch oil extract.

The invention having been hereinabove described, it will be obvious that the same be varied in many ways. Those skilled in the art recognize that other and further changes and modifications may be made thereto without departing from the spirit of the invention, and it is intended that all such changes and modifications fall within the scope of the invention, as defined in the appended claims.

What is claimed is:

1. A gel matrix for topical use on a subject having an epithelial surface to be immersed in water, said epithelial surface comprising mucus, mucosa or skin surface, the gel matrix comprising:
   about 15% w/w polyethylene glycol-150/decyl alcohol/saturated dicyclohexyl-methane diisocyanate copolymer, which confers to said matrix the characteristics of being insoluble but dispersible in water, and capable of adhering to said epithelial surface,
   about 37.4% to 45% w/w ethoxydiglycol,
   1-6% w/w polysorbate surfactant,
   a liquid carrier which is bio-compatible with said epithelial surface, the gel matrix having a viscosity, before application, of about 35-55 centipoises.

2. The gel matrix of claim 1, which further comprises a medication.

3. The gel matrix of claim 2, wherein said medication is active towards a causative agent or a symptom affecting said surface.

4. The gel matrix of claim 3, wherein said medication is one or more anti-ulcer, anti-microbial, anti-histaminic, anti-inflammatory, soothing, wound healing, anti-oxidant, sun screen, anti-UVs, anti-cancer, anesthetic and analgesic agents.

5. The gel matrix of claim 2, wherein said medication is an organic oil.

6. The gel matrix of claim 5, wherein said oil is a plant extract.

7. The gel matrix of claim 6, wherein said plant oil extract has anti-infectious properties.

8. The gel matrix of claim 7, wherein said plant oil is pine, clove, coriander or Sweet Birch oil.

9. The gel matrix of claim 8, wherein said oil is present in a final concentration of 1-5% (w/w).

10. The gel matrix of claim 5, which further comprises an anti-oxidant.

11. The gel matrix of claim 1, which comprises 15% (w/w) polyethylene glycol-150/decyl alcohol/saturated dicyclohexyl-methane diisocyanate copolymer.

12. The gel matrix of claim 11, which has the following composition by weight: polyethylene glycol-150/decyl alcohol/saturated dicyclohexylmethane diisocyanate copolymer 15%, ethoxydiglycol 37.4-45%, oil 1-5% and polysorbate 20 1-6%, demineralised water 41.17%, propyl gallate 0.1%, sodium metabisulfite 0.25%, sodium carbonate 0.05%, dye yellow 5 LK (14-16%) 0.50%.

13. A method of using a gel matrix according to claim 1, said method comprising topically applying said gel matrix on the epithelial surface of the subject.

14. A method according to claim 13, wherein the subject is a fish.

15. A method according to claim 13, wherein the gel matrix comprises 15% (w/w) polyethylene glycol-150/decyl alcohol/saturated dicyclohexyl-methane diisocyanate copolymer.

16. A method according to claim 13, wherein said gel further comprises a medication.

17. A method according to claim 16, wherein said medication is one or more anti-ulcer, anti-microbial, anti-histaminic, anti-inflammatory, soothing, wound healing, anti-oxidant, sun screen, anti-UVs, anti-cancer, anesthetic and analgesic agents.

18. A method according to claim 16, wherein said medication is an organic oil extracted from a plant.

19. A method according to claim 18, wherein said organic plant oil extract is pine, clove, coriander or Sweet Birch oil.

* * * * *